United States Patent [19]

Garlick, Jr. et al.

[11] Patent Number: 5,695,746
[45] Date of Patent: Dec. 9, 1997

[54] LIQUID DENTIFRICE WITH MOUTHWASH FRESH TASTE

[75] Inventors: Theodore Harrison Garlick, Jr., Litchfield; David Robert Williams, Monroe; Alexander George Ziemkiewicz, Shelton, all of Conn.

[73] Assignee: Chesebrough-Pond's USA Co., Division of Conopco, Inc., Greenwich, Conn.

[21] Appl. No.: 508,768

[22] Filed: Jul. 28, 1995

[51] Int. Cl.$^6$ .................... A61K 7/16; A61K 7/26
[52] U.S. Cl. .................... 424/49; 424/58
[58] Field of Search .................... 424/49–58

[56] References Cited

U.S. PATENT DOCUMENTS

| | | |
|---|---|---|
| 3,506,757 | 4/1970 | Salzmann . |
| 4,469,673 | 9/1984 | Ioka . |
| 4,574,081 | 3/1986 | Shymon . |
| 5,275,803 | 1/1994 | Dawson . |
| 5,298,238 | 3/1994 | Barcelon et al. . |
| 5,310,543 | 5/1994 | Dawson . |

FOREIGN PATENT DOCUMENTS

| | | |
|---|---|---|
| 1086420 | 5/1994 | China . |
| 338978 | 10/1989 | European Pat. Off. . |
| 64835 | 3/1994 | Hungary . |
| 52125639 | 10/1977 | Japan . |
| 03067560 | 3/1991 | Japan . |
| 321765 | 3/1970 | Sweden . |
| 2068730 | 5/1984 | United Kingdom . |
| 2 240 473 | 1/1991 | United Kingdom . |
| 9308792 | 5/1993 | WIPO . |

OTHER PUBLICATIONS

Arctander Perfume and Flavor Chemicals entire Menthol Anethole (1969).
Abstr. Gwartney et al. Jl. Sensory Studies 10(4): 393–400 (1995).
Abstr. Cliff et al. Physiology & Behavior 56(5): 1021–1029 Nov. 1994.
Abstr. Jay et al. J. Food Sci. 6(2):129–139 CA. 101:169269 1000ppm M (1984).
Abstr. CA. 125:95619 of WO/PCT 9615770 May 1996 Leung (Warner Taubert) .068M .013A.
Abstr. CA. 124:270035 Y/N CN 1/11123 Nov. 1995 .02–0.1M.

*Primary Examiner*—Shep K. Rose
*Attorney, Agent, or Firm*—Milton L. Honig

[57] ABSTRACT

A liquid dentifrice is provided which includes a humectant, an abrasive, a structuring thickener and a specified level of menthol. Sufficient menthol in amounts greater than 0.5 up to 2% by weight are incorporated to achieve a freshened breath real mouthwash impact.

14 Claims, No Drawings

LIQUID DENTIFRICE WITH MOUTHWASH FRESH TASTE

BACKGROUND OF THE INVENTION

1. Field of the Invention

The present invention relates to a liquid dentifrice composition with flavor impact similar to a mouthwash for freshening breath.

2. The Related Art

Liquid dentifrices have been commercially available for many years. Perhaps the best known of these products in the U.S. market is Pearl Drops®, sold by Carter Wallace, Inc. of New York. The product has long been advertised as a whitening toothpolish with cavity fighting fluoride protection. Check.Up®, a former commercially available liquid toothpaste, was advertised for its brushing convenience, cavity prevention protection and similarity to a mouthrinse.

Of course, there also is a considerable body of patent literature on liquid dentifrices. Many inventions have focused upon the problem of stably suspending particulate abrasive material. Illustrative is the technology reported in U.S. Pat. No. 5,310,543 (Dawson), U.S. Pat. No. 5,275,803 (Dawson), U.S. Pat. No. 3,506,757 (Salzmann) and GB 2,240,473 (Lion) focusing on the use of xanthan and other polysaccharide gums as suspending agents.

Only perfunctory attention has been given to developing flavor impact, especially impact associated with menthol. Where the term "flavor (or flavour)" appears, often there has been little or no description as to the chemical components. Non-liquid dentifrice compositions which have focused upon flavors, such as U.S. Pat. No. 5,186,926 (Williams et al.) have exemplified menthol at total levels no higher than 0.5%.

Close.Up®, a commercial non-liquid dentifrice sold by Chesebrough-Pond's U.S.A., has for many years been advertised as a paste or gel with "real mouthwash". Menthol levels in this product are below 0.5%.

An object of the present invention is to provide a liquid dentifrice with a real mouthwash flavor impact to deliver a tingling fresh sensation.

Another object of the present invention is to provide a liquid dentifrice with a real mouthwash flavor impact within a clear gel composition.

These and other objects of the present invention will become more readily apparent from consideration of the following summary, detailed description and examples.

SUMMARY OF THE INVENTION

A liquid dentifrice is provided which includes:

(i) from 25 to 90% by weight of a humectant;
(ii) from 5 to 50% by weight of an abrasive;
(iii) from 0.05 to 10% by weight of a structuring thickener;
(iv) from greater than 0.5 to 2% by weight of menthol; and wherein the liquid dentifrice has a viscosity between 50 and 500 Pa.s at 25° C. under a shear rate of 0.1 sec.$^{-1}$.

DETAILED DESCRIPTION OF THE INVENTION

We have found that flavor release in a liquid dentifrice has a totally different profile than that from the traditional (and considerably more viscous) toothpastes and dentifrice gels. This is especially so with the menthol flavor component.

Now it has been determined that considerably more menthol must be formulated into liquid dentifrices than ordinarily utilized with pastes and gels to achieve a mouthwash impact effect. Taste testing panelists have colloquially referred to this impact as a "wow!" mouthfeel indicating a freshened breath.

Achievement of the proper freshness impact requires from more than 0.5 up to 2% by weight of menthol, preferably from 0.75 to 1.5%, optimally from 0.8 to 1.3%. For purposes of this invention, the aforementioned concentration ranges include the total amount of menthol added to the formula as well as any menthol amounts delivered from additional flavor adjuncts (e.g. from spearmint and peppermint).

Anethole can also be included in the liquid dentifrices of the present invention. Anethole through its sweetness overcomes the bitterness aspects of menthol. Relative weight concentrations of menthol to anethole may range from about 100:1 to 1:1, preferably 50:1 to 2:1, more preferably 30:1 to 5:1, optimally from 28:1 to 10:1.

A humectant and water system will normally be included in the liquid dentifrices of this invention. Humectants are usually polyols which, for example, may include glycerin, sorbitol, propylene glycol, lactitol, xylitol, polypropylene glycol, polyethylene glycol, hydrogenated corn syrup and mixtures thereof. Most preferred is a mixture of Polyol II (CTFA name for sorbitol), Polyol III (CTFA name for sorbitol and related polyols) and glycerin. Generally the amount of humectant will range from 25 to 90%, preferably from 50 to 70% by weight. Particularly preferred is a liquid mixture of 3 to 30% water, 0 to 80% glycerin and/or 20 to 80% sorbitol.

An abrasive is another component of compositions according to the present invention. Abrasives may be selected from water-insoluble alkali or alkaline earth metal salts of metaphosphate (IMP), calcium carbonate (chalk), sodium bicarbonate, aluminates and silicates.

Abrasives which are useful especially in clear dentifrices are the silica xerogels described in U.S. Pat. No. 3,538,230 (Pader et al.). In fact, silica xerogels are the abrasives of choice for use in clear dentifrices and are preferred abrasives in the present invention. Silica xerogels yield dentifrice compositions which result in surprisingly good cleaning and polishing characteristics when applied topically to the teeth. In addition, silica xerogels produce a high luster without excessive enamel or dentin abrasion. These silicas are also highly compatible with most common dentifrice ingredients, including oral health agents, and may be formulated to produce transparent or translucent pastes.

More specifically, the silica xerogels useful in the present dentifrice compositions are synthetic, amorphous, porous silica xerogels having an average particle diameter in the range from 2 to 30 microns, preferably in the range from 3 to 15 microns.

Silica xerogels suitable for use in clear dentifrice compositions are commercially available. One suitable xerogel is marketed under the trade name Syloid 63X. This material has an average particle diameter of 8 to 10 microns.

Other suitable silicas include Syloid 63, which has an average particle diameter of about 5 microns, Syloid 73, which has an average particle diameter of about 5 microns, Syloid 63XX, which has an average particle size of about 10 microns, and Syloid 404, which has an average particle diameter of about 6 microns. All of the above silica xerogels in the Syloid series are available from W. R. Grace, Davison Chemical Division.

The amount of abrasive is limited to those amounts which safely provide good polishing and cleaning and which, when combined with common toothpaste ingredients of a non-abrasive nature, will give a smooth, flowable, not excessively gritty, acceptable tasting toothpaste. This amount generally lies in the range of 5% to 50% by weight of the total dentifrice. The preferred range is from 6 to 35% and the most preferred range is 7 to 25% by weight of the dentifrice.

Organic and inorganic structuring thickeners may be included in liquid dentifrice compositions of the present invention. Prime among inorganic structuring thickeners is finely ground colloidal silica known also as an aerogel, an example of which is Syloid 244 or Sylox 15X available from W. R. Grace. Precipitated silicas may also be applicable. In the broadest terms, these silicas are prepared by admixture of a mineral acid and sodium silicate solution to form a precipitate followed by washing, drying and milling of the precipitate. The products are amorphous, hard particles which can be made with differing degrees of abrasivity. One such precipitated silica is disclosed in U.S. Pat. No. 4,272,509 (Wason). Another type of precipitated silica which can be used, but which has only limited abrasive properties, is disclosed in U.S. Pat. No. 3,864,470 (Wason). The description of precipitated silicas and the methods of their preparation are disclosed in U.S. Pat. Nos. 4,272,509 and 3,864,470. A most preferred commercially available precipitated silica is Zeo 49 available from the J. M. Huber Corporation, Chemicals Division. Amounts of the inorganic structuring thickeners may range from 0.5 to 10%, preferably from 1 to 5%, optimally from 1.5 to 3.0% by weight.

Organic thickeners suitable for the present invention include hydroxypropyl methylcellulose, hydroxyethyl cellulose, sodium carboxymethyl cellulose, xanthan gum, guar gum, tragacanth gum, karaya gum, arabic gum, Irish moss, starch, alginate and carrageenan. Most preferred are the polysaccharide gums, especially xanthan and guar gums. Amounts or organic thickeners may range from 0.1 to 2%, preferably from 0.3 to 1.5%, optimally from 0.5 to 0.8% by weight.

Water may be present in the liquid dentifrice composition in amounts ranging from 2 to 70%, preferably from 30 to 55%, optimally from 30 to 50% by weight.

Small amounts of ethanol may also be present in the liquid dentifrice compositions. These amounts may range from 0.5 to 8%, preferably from 1 to 5%, optimally from 1.5 to 3.5% by weight.

Surfactants are also normally included in liquid dentifrice compositions. These surfactants may be of the anionic, nonionic, cationic or amphoteric type. Most preferred are sodium lauryl sulfate, sodium dodecyl benzene sulfonate and sodium lauryl sarcosinate. Surfactants are usually present in an amount from about 0.2 to 8%, preferably from 0.5 to 5%, optimally from 1 to 2% by weight.

Tartar control agents may be incorporated into compositions of this invention, especially effective will be agents containing phosphorous or zinc. Inorganic phosphorous tartar control agents may include pyrophosphates such as disodium pyrophosphate, dipotassium pyrophosphate, tetrapotassium pyrophosphate, tetrasodium pyrophosphate and mixtures thereof. Organic phosphorous and zinc compounds that may serve as tartar control agents include zinc citrate and polyphosphonates such as disodium ethane-1-hydroxy-1,1-diphosphonate (EHDP), methanediphosphonic acid and 2-phosphonobutane-1,2,4-tricarboxylic acid. Levels of the tartar control agents may range from 0.1 to 10%, preferably from 0.5 to 8%, optimally from 1 to 5% by weight.

For anticaries protection, a source of fluoride ion will normally be present in the second component of the dentifrice composition. Fluoride sources include sodium fluoride, potassium fluoride, calcium fluoride, stannous fluoride, stannous monofluorophosphate and sodium monofluorophosphate. These sources should release anywhere from 25 to 2500 ppm of fluoride ion. The anticaries agent will be present in an amount from 0.05 to 3% by weight, preferably 0.2 to 1% by weight of the second component.

Sweetening agents such as sodium saccharin, sodium cyclamate, Acesulfan K, aspartame, sucrose and the like may be included at levels from about 0.1 to 5% by weight.

Other additives may also be incorporated including preservatives, silicones, other synthetic or natural polymers such as Gantrez S-97, and antigingivitis actives such as triclosan.

Furthermore, where it is desired to have an opaque toothpaste, titanium dioxide or some opacifier agent may be incorporated into the otherwise transparent or translucent gel.

Colorants may often be included in compositions of this invention. Typical colorants are D&C Yellow No. 10, FD&C Blue No. 1, FD&C Red No. 40, D&C Red No. 33 and combinations thereof. Levels of the colorant may range from 0.0001 to 0.1, preferably from 0.001 to 0.01% by weight.

Compositions of the present invention should have a viscosity of at least 50 Pa.s (at 25° C. under a shear of 0.1 sec$^{-1}$) to "hold" on standard toothbrush bristles for at least 5 minutes, and should have a viscosity of no more than 500 Pa.s (at 25° C. under a shear of 0.1 sec$^{-1}$) to enable easy manufacture, filling and dispensing from suitable containers. Preferably, the viscosity may range from 100 to 400 Pa.s.

Liquid dentifrice compositions of the present invention are characterized not only by viscosity but also by having cohesion levels of less than 25 grams, usually between 0 and 10 grams. Common toothpaste and gels ordinarily have a cohesion greater than 100 grams. Cohesion is measured on an Tensile Tester wherein the sampled dentifrice is placed between two 1-inch round plates having a 4.0 mm gap. As the two plates separate, the dentifrice resists deformation. The forcing grams required to pull the plates apart is noted as the measure of cohesion.

Liquid dentifrice compositions of the present invention advantageously are also clear. The method for assessing clarity involves use of a standard chart consisting of black symbols varying in size on a white background. This is the RIT Alphanumeric Resolution Test Object RT 4-74, produced by Graphics Arts Research Center, Rochester Institute of Technology. The ability to discern the symbols clearly through a sample of product of standard thickness is measured. The symbols are assigned numbers from −12 to +13. The higher, more positive number, the greater the clarity. If even the most prominent symbol cannot be readily defined through the layer of toothpaste, the toothpaste is considered cloudy and not translucent. In practice, products with a numerical rating of about −12 or higher are considered translucent.

The term "gel" as used herein includes not only those compositions which are gels in the strict technical sense but also gel-like compositions which have the same feeling and appearance of gels.

The following examples will more fully illustrate embodiments of this invention. All parts, percentages and proportions referred to herein and in the appended claims are by weight unless otherwise indicated.

EXAMPLES 1–4

Four formulations typical of the present invention are described in Table I. The respective examples illustrate Antitartar, Cool Mint Blue, Original Red and Baking Soda variants of a liquid gel according to the present invention.

TABLE I

| TRADE NAME | CHEMICAL OR CTFA NAME | EXAMPLE (WEIGHT %) | | | |
|---|---|---|---|---|---|
| | | 1 | 2 | 3 | 4 |
| Polyol II (70%) | Sorbitol | 33.81 | 33.81 | 33.81 | 33.81 |
| Polyol III (75%) | Sorbitol and related Polyols | 27.19 | 27.19 | 27.19 | 27.19 |
| Syloid 63XX | Hydrated Silica | 18.00 | 18.00 | 18.00 | 18.00 |
| Syloid 244 | Hydrated Silica | 3.00 | 3.00 | 3.00 | 3.00 |
| Glycerin | Glycerin | 2.76 | 2.76 | 2.76 | 2.76 |
| Ethanol | Ethanol | 2.58 | 2.58 | 2.58 | 2.58 |
| Zinc Citrate | Zinc Citrate | 2.00 | — | — | — |
| Sodium Lauryl Sulfate | Sodium Lauryl Sulfate | 1.54 | 1.54 | 1.54 | 1.54 |
| Menthol USP-Natural | Menthol | 1.30 | 1.30 | 1.10 | 1.08 |
| Flavor | Flavor | 0.55 | 0.55 | 0.60 | 0.34 |
| Keltrol | Xanthan Gum | 0.55 | 0.55 | 0.55 | 0.55 |
| Sodium Saccharin | Sodium Saccharin | 0.47 | 0.47 | 0.47 | 0.47 |
| Sodium Fluoride | Sodium Fluoride | 0.23 | 0.23 | 0.23 | 0.23 |
| Sodium Benzoate | Sodium Benzoate | 0.09 | 0.09 | 0.09 | 0.09 |
| D&C Yellow #10 | C.I. 47005 | 0.005 | — | — | — |
| FD&C Blue #1 | C.I. 42090 | 0.005 | 0.005 | — | — |
| FD&C Red #40 | C.I. 16035 | — | — | 0.005 | — |
| D&C Red #33 | C.I. 17200 | — | — | 0.005 | — |
| Baking Soda | Sodium Bicarbonate | — | — | — | 0.50 |
| Titanium Dioxide | C.I. 77891 | — | — | — | 0.20 |
| Water | | bal. | bal. | bal. | bal. |

EXAMPLE 5

Critical menthol levels for incorporation into the Example 2 and 4 liquid dentifrice formulations were evaluated by a pair of experienced flavorists.

Testing involved brushing with approximately 0.5 grams of the liquid dentifrice for about 20 seconds. The flavorists then expectorated the dentifrice and described the flavor before rinsing with water. Increasing levels of added menthol in increments of 0.1% were added to the respective formulations. Approximately six evaluations were performed per hour.

Four critical attributes and an overall Effect were determined. The attributes included cooling, freshness, bitterness and burning. Total flavor Effect was also noted (i.e. overall organoleptic impression). As a comparison point, the flavorists employed Arm & Hammer Original Baking Soda product which had been identified through previous sensory work to be the highest scoring, significant U.S. toothpaste product for this family of attributes. Tables II and III set forth the results of the Cool Mint Blue and Baking Soda variants, Example 2 and 4, respectively.

TABLE II

COOL MINT BLUE*

| TOTAL MENTHOL | TOTAL ORGANO-LEPTIC EFFECT | COOL-ING | FRESH-NESS | BITTER | BURN-ING |
|---|---|---|---|---|---|
| 0.5% | low | low | low | no | no |
| 0.6% | low | medium | medium | no | no |
| 0.7% | low | medium | medium | no | no |
| 0.8% | medium | medium | medium | no | no |
| 0.9% | medium | medium | medium | no | no |
| 1.0% | medium | medium | medium | no | no |
| 1.1% | medium | medium | medium | no | no |
| 1.2% | medium | high | high | no | no |
| 1.3% | high | high | high | no | no |
| 1.4% | high | high | high | yes | yes |
| 1.5% | high | high | high | yes | yes |

*Menthol to Anethole weight ratio 10:1.

TABLE III

BAKING SODA VARIANT*

| TOTAL MENTHOL | TOTAL ORGANO-LEPTIC EFFECT | COOL-ING | FRESH-NESS | BITTER | BURN-ING |
|---|---|---|---|---|---|
| 0.5% | low | medium | medium | no | no |
| 0.6% | medium | medium | medium | no | no |
| 0.7% | medium | medium | medium | no | no |
| 0.8% | medium | medium | medium | no | no |
| 0.9% | medium | medium | high | no | no |
| 1.0% | medium | high | high | no | no |
| 1.1% | high | high | high | no | no |
| 1.2% | high | high | high | yes | yes |
| 1.3% | high | high | high | yes | yes |
| 1.4% | high | high | high | yes | yes |
| 1.5% | high | high | high | yes | yes |

*Menthol to Anethole weight ratio 10:1.

Flavor results shown in Table II and III indicate that more than 0.5% menthol is necessary to achieve at least a medium total organoleptic Effect. At 1.4% total menthol, the formulations left an unacceptably bitter and burning sensation.

The foregoing description and Examples illustrate selected embodiments of the present invention. In light thereof various modifications will be suggested to one skilled in the art, all of which are within the spirit and purview of this invention.

What is claimed is:

1. In a liquid dentifrice comprising:
   (i) from 25 to 90% by weight of a humectant;
   (ii) from 5 to 50% by weight of an abrasive:
   (iii) from 0.5 to 10% by weight of a structuring thickener;
   (iv) from greater than 0.7 to 1.3% by weight of menthol;
   the liquid dentifrice having a viscosity between 50 and 500 Pa.s at 25° C. under a shear rate of 0.1 sec$^{-1}$, wherein the improvement comprises the composition including an effective amount of anethole which through its sweetness overcomes the bitterness of menthol and whereby cooling and freshness attributes of menthol are maintained without bitterness or burning.

2. The dentifrice according to claim 1 wherein menthol is present in an amount from 0.75 to 1.1% by weight.

3. The dentifrice according to claim 1 wherein menthol is present in an amount from 0.8 to 1.3% by weight.

4. The dentifrice according to claim 2 wherein the structuring thickener is colloidal silica present at a level from 1 to 5% by weight.

5. The dentifrice according to claim 1 further comprising from 0.1 to 2% of xanthan gum.

6. The dentifrice according to claim 1 wherein the dentifrice has a cohesion between 0 and less than 25 grams.

7. The dentifrice according to claim 1 wherein the dentifrice is clear.

8. The dentifrice according to claim 1 wherein the dentifrice is a gel.

9. The dentifrice according to claim 7 which is opacified with titanium dioxide.

10. The dentifrice according to claim 1 further comprising anethole in an amount of menthol to anethole ranging form 50:1 to 10:1.

11. In a method for Imparting a real mouthwash flavor impact through use of a non-mouthwash liquid dentifrice composition, the method comprising:

(a) delivering onto a brush a liquid dentifrice composition comprising:
 (i) from 25 to 90% by weight of a humectant;
 (ii) from 5 to 50% by weight of an abrasive;
 (iii) from 0.5 to 10% by weight of a structuring thickener:
 iv) from greater than 0.7 to 1.3% by weight of menthol; and wherein the liquid dentifrice has a viscosity between 50 and 500 Pa.s at 25° C. under a shear rate of 0.1 sec$^{-1}$; and (b) brushing teeth with the liquid dentifrice, wherein the improvement comprises the composition including an effective amount of anethole which through its sweetness overcomes the bitterness of menthol and whereby cooling and freshness attributes of menthol are maintained without bitterness or burning.

12. The dentifrice according to claim 1 further comprising anethole in an amount of menthol to anethole ranging from 28:1 to 10:1.

13. The method according to claim 11 wherein the composition further comprises anethole in an amount of menthol to anethole ranging from 50:1 to 10:1.

14. The method according to claim 11 wherein the composition further comprises anethole in an amount of menthol to anethole ranging from 28:1 to 10:1.

* * * * *